United States Patent [19]

Ichihashi et al.

[11] Patent Number: 4,575,572

[45] Date of Patent: Mar. 11, 1986

[54] METHOD FOR PRODUCING CYCLOOLEFINS

[75] Inventors: Hiroshi Ichihashi; Hiroshi Yoshioka, both of Niihama, Japan

[73] Assignee: Sumitomo Chemical Company, Limited, Osaka, Japan

[21] Appl. No.: 753,861

[22] Filed: Jul. 11, 1985

[30] Foreign Application Priority Data

Jul. 31, 1984 [JP] Japan ............................ 59-162738
Nov. 16, 1984 [JP] Japan ............................ 59-243083
Nov. 20, 1984 [JP] Japan ............................ 59-245668

[51] Int. Cl.$^4$ ................................................ C07C 5/11
[52] U.S. Cl. ............................ 585/266; 585/267; 585/273; 585/274; 585/276
[58] Field of Search ............... 585/266, 267, 273, 274, 585/276

[56] References Cited

U.S. PATENT DOCUMENTS 3,391,206 7/1968 Beek ..................................... 585/273
4,225,733 9/1980 Kameyama et al. ................. 585/266
4,392,001 7/1983 Don et al. ............................ 585/273
4,503,249 3/1985 Nowack et al. ..................... 585/274

FOREIGN PATENT DOCUMENTS 764502 8/1957 Canada ................................. 585/266
3046939 10/1976 Japan ................................... 585/266
9186932 4/1983 Japan ................................... 585/273

Primary Examiner—John Doll
Assistant Examiner—A. Pal
Attorney, Agent, or Firm—Stevens, Davis, Miller & Mosher

[57] ABSTRACT

A method for producing cycloolefins useful as an intermediate material for lysine, caprolactam, adipic acid, medicines, agricultural chemicals, dyes and the like, which comprises partial hydrogenation of aromatic hydrocarbons with hydrogen gas in the presence of a catalyst composed of barium sulfate which is a carrier as well as ruthenium and at least one metal selected from the group consisting of iron, cobalt, silver and copper supported on said barium sulfate, and water.

21 Claims, No Drawings

METHOD FOR PRODUCING CYCLOOLEFINS

The present invention relates to a method for producing cycloolefins by the partial hydrogenation of the corresponding aromatic hydrocarbon compounds.

Cycloolefins are useful as an intermediate material for lysine, caprolactam, adipic acid, medicines, agricultural chemicals and the like. For producing cycloolefins, many methods such as dehydration of cyclohexanols, dehydrohalogenation of halogenated cyclohexanes, cracking of cyclohexylallenes, dehydrogenation or oxidative dehydrogenation of cyclohexanes, and the like are so far well known.

It is well known that to obtain cycloolefins in good yields by the partial hydrogenation of aromatic hydrocarbon compounds is difficult because the cycloolefin produced by this reaction is generally easier to be hydrogenated than the aromatic hydrocarbon compound used as a material.

If, however, cycloolefins can be obtained with good yields by the partial hydrogenation of aromatic hydrocarbon compounds, the process of this method is the most simplified one, being desirable also from the industrial point of view.

The well-known methods for producing cycloolefins by the partial hydrogenation of aromatic compounds are as follows:

(1) Partial hydrogenation in the presence of water, an alkali agent and a reduced catalyst formed from the compound of a metal belonging to Group VIII of the periodic table [U.S. Pat. No. 3,767,720].
(2) Partial hydrogenation in the presence of water and a ruthenium catalyst dispersed in silica gel derived from the hydrolyzate of silicon alkoxide [Japanese Patent Application Kokai (Laid-open) No. 155328/1984].
(3) Partial hydrogenation in the presence of water, cobalt sulfate and a catalyst composed mainly of ruthenium supported on a metal oxide such as silica, alumina, etc. [Japanese Patent Application Kokai (Laid-open) No. 130926/1982].
(4) Partial hydrogenation in the presence of water and a catalyst produced by treating a solid catalyst composed mainly of at least one of ruthenium and rhodium with an aqueous solution containing the salt of a cation [Japanese Patent Application Kokai (Laid-open) No. 98243/1976].
(5) Partial hydrogenation under neutral or acid conditions in the presence of water and a catalyst composed of ruthenium and at least one of iron, cobalt, nickel, chromium, tungsten and molybdenum supported on alumina or zinc aluminate (U.S. Pat. No. 3,912,787).
(6) Partial hydrogenation in the presence of a catalyst composed of ruthenium supported on a compound containing at least one rare earth element [Japanese Patent Application Kokai (Laid-open) No. 186932/1984].

The method (1) not only requires a very complicated reaction system, but also has problems in terms of the isolation of reaction products and corrosion of reactors by a chlorine ion. This method, therefore, may not always be said to be satisfactory in industry. The method (2) requires a complicated catalyst preparation process and has problems in terms of the reproducibility of catalytic performance. The methods (3), (4) and (5) give no sufficient selectivity and yield. The method (6) produces cyclohexene in relatively good yields, but it absolutely requires addition of large amounts of alkali agent to the reaction system. As described above, it was difficult to industrialize any of these well-known methods.

An object of the present invention is to provide a method for producing cycloolefins in an industrially advantageous manner by overcoming the defects of these prior-art techniques. In order to attain this object, the present inventors extensively studied and found a novel catalyst suitable to produce cycloolefins by the partial hydrogenation of the corresponding aromatic hydrocarbons. The present inventors thus attained to the present invention.

According to the present invention, there are provided the following methods:

(1) A method for producing cycloolefins which comprises partial hydrogenation of aromatic hydrocarbons with hydrogen gas in the presence of a catalyst composed of barium sulfate which is a carrier as well as ruthenium and at least one metal selected from the group consisting of iron, cobalt, silver and copper supported on said barium sulfate, and water;
(2) a method for producing cycloolefins which comprises partial hydrogenation of aromatic hydrocarbons with hydrogen gas in the presence of a catalyst composed of barium sulfate which is a carrier as well as ruthenium and at least one metal selected from the group consisting of iron, cobalt, silver and copper supported on said barium sulfate, an additive comprising the sulfate of at least one metal selected from the group consisting of lithium, cobalt, iron and zinc, and water; and
(3) a method for producing cycloolefins which comprises partial hydrogenation of aromatic hydrocarbons with hydrogen gas in the presence of a catalyst composed of barium sulfate which is a carrier and ruthenium supported thereon, an additive comprising the sulfate of at least one metal selected from the group consisting of lithium, cobalt, iron and zinc, and water.

The method of the present invention will be illustrated in more detail hereinafter.

The aromatic hydrocarbon used in the present invention is benzene, toluene, xylene and lower alkylbenzenes. It need not have particularly a high purity and may contain cycloparaffins, lower paraffin hydrocarbons, etc.

The catalyst used in the present invention is one composed of barium sulfate which is a carrier as well as ruthenium alone or ruthenium and at least one metal selected from the group consisting of iron, cobalt, silver and copper supported on said barium sulfate. The catalyst is prepared according to the commonly used methods for producing the usual supported metal catalysts. For example, the following well-known impregnation/-supporting methods are preferably used: An evaporation-to-dryness method wherein barium sulfate is impregnated with a solution containing a compound of the above metal and the solvent is evaporated with stirring to fix the compound to the carrier; a spraying method wherein a solution containing a compound of the above metal is sprayed onto barium sulfate kept in a dry state; a method wherein barium sulfate is impregnated with a solution containing a compound of the above metal and filtered off; and the like.

The compound of ruthenium includes for example the halide, nitrate, hydroxide and oxide of ruthenium, complexes such as ruthenium carbonyl, ruthenium ammine complex, etc.; ruthenium alkoxide and the like.

The compounds of iron, cobalt, silver and copper include the halide, nitrate, etc. of each metal.

The solvent for the solution containing the above metal compound includes water and organic solvents such as alcohol, acetone, tetrahydrofuran, etc. These solvents may be used alone or in combination.

By reducing the carrier-supported metal compound prepared by the above method, the desired supported metal catalyst is obtained. The reducing agent includes hydrogen, carbon monoxide, alcohol vapor, hydrazine, sodium borohydride, formalin and other well-known reducing agents.

When hydrogen is used, a reduction temperature within a range of 150° to 450° C., preferably 180° to 300° C. is selected. When the temperature is less than 150° C., the reduction of ruthenium compounds is not sufficient. When the temperature is more than 400° C., supported ruthenium agglomerates to cause reduction in the surface area of metal and denaturation of the catalyst surface, and this leads to lowering in the activity and selectivity to form cycloolefins. The amount of ruthenium supported is within a range of 0.01 to 20 wt. %, preferably 0.1 to 10 wt. % based on the carrier.

When iron or cobalt is used as a co-supported component, its atomic ratio to ruthenium is within a range of 0.1 to 15.0, preferably 0.5 to 5.0. When copper or silver is used as such component, its atomic ratio to ruthenium is within a range of 0.05 to 5.0, preferably 0.1 to 1.0.

The present invention is characterized in that barium sulfate is used as a carrier for catalyst. The reason for this is that the selectivity of reaction is markedly improved by the use of barium sulfate as shown in the examples and comparative examples. The working mechanism of barium sulfate is considered as follows: Considering that barium sulfate gives markedly improved yields of cycloolefins as compared with metal oxides (e.g. silica, alumina) generally used as a carrier, barium sulfate has not only a simple effect to increase the effective surface area of metal, but also a great control over the property of active points of catalyst.

In the method of the present invention, water is added to the reaction system. Since the catalyst is located in aqueous layer, water not only acts to facilitate separation of the catalyst from the reaction product in the organic layer, but also has a great effect to increase the selectivity to cycloolefins. The amount of water added is selected from a range of generally 0.01 to 10 times by volume, preferably 0.1 to 5 times by volume based on the aromatic hydrocarbon.

In the present invention, when an aqueous solution containing the sulfate of at least one metal selected from the group consisting of lithium, cobalt, iron and zinc, is used as an additive, the amount of said sulfate is within a range of 1:1 to 1:500, preferably 1:5 to 1:250 in an atomic ratio to ruthenium present in the catalyst used for reaction. As shown in the examples hereinafter, when barium sulfate is used as a carrier and said metal sulfate is used as an additive, cycloolefins can be obtained in particularly high yields.

The hydrogen pressure on reaction is selected from a range of generally 0.1 to 20 MPa, preferably 0.5 to 10 MPa. High pressures exceeding 20 MPa are uneconomical from the industrial point of view, and pressures below 0.1 MPa lower the reaction rate, being uneconomical also in terms of equipment.

The reaction temperature is selected from a range of generally 50° to 250° C., preferably 100° to 200° C. Temperatures exceeding 250° C. lower the selectivity of cycloolefins, and temperatures below 50° C. unpreferably lower the reaction rate.

The form of reaction of the present invention is not particularly limited, and any of a batchwise process with one or more reaction vessels and a continuous process may be used.

According to the present invention, cycloolefins are obtained in high yields, the reaction operation is simple and corrosion of equipments does not occur easily, so that it becomes possible to produce cycloolefins advantageously in industry.

The present invention will be illustrated more clearly with reference to the following examples and comparative examples, but it is not limited to these examples only.

Hereupon, the conversion, yield and selectivity used in the examples and comparative examples are defined by the following equations.

$$\text{Conversion (\%)} = \frac{\text{Number of moles of aromatic hydrocarbon consumed by reaction}}{\text{Number of moles of aromatic hydrocarbon used in reaction}} \times 100$$

$$\text{Yield (\%)} = \frac{\text{Number of moles of produced cycloolefin}}{\text{Number of moles of aromatic hydrocarbon used in reaction}} \times 100$$

$$\text{Selectivity (\%)} = \frac{\text{Yield of cycloolefin}}{\text{Conversion of aromatic hydrocarbon}} \times 100$$

EXAMPLE 1

0.190 Gram of $RuCl_3.3H_2O$ was added to a 500 cc eggplant-form flask, and 200 cc of water was added to dissolve it. After adding 3.6 g of $BaSO_4$, the flask was mounted on a rotary evaporator. The $BaSO_4$ was impregnated with the aqueous solution with stirring at room temperature for 1 hour, and then at 60° C. for 1 hour. Thereafter, water was evaporated at 80° C. under reduced pressure.

The dried-up product obtained was filled in a Pyrex glass tube of 5 mm in inside diameter, heated to 200° C. while passing hydrogen gas therethrough at a rate of 100 ml/min and kept at this temperature for 4 hours to activate the catalyst. The composition of the catalyst obtained was 2% $Ru/BaSO_4$.

A solution of 0.5 g of $Li_2SO_4.H_2O$ in 15 cc of water was added to a 100 ml stainless steel autoclave of which the atmosphere was thoroughly replaced by argon in advance, and then 100 mg of the above catalyst and 15 cc of benzene were added in this order. Thereafter, hydrogen gas was introduced, and reaction was carried out at 180° C. for 3 hours with stirring under a reaction pressure of 4.0 MPa.

After completion of the reaction, the oily layer was taken out, and the product was analyzed by gas chromatography to obtain the result: Conversion of benzene, 59.1%; selectivity of cyclohexene, 23.0%; and yield of cyclohexene, 13.6%.

Hereupon, a reaction product other than cyclohexene was cyclohexane only.

COMPARATIVE EXAMPLE 1

Procedure was carried out in the same manner as in Example 1 except that γ-form alumina was used in place of $BaSO_4$ in the step of catalyst. preparation, to produce 2% $Ru/\gamma-Al_2O_3$ catalyst. Using this catalyst, partial hydrogenation of benzene was carried out for 3 hours in the same manner as in Example 1 to obtain the result: Conversion of benzene, 67.8%; selectivity of cyclohexene, 8.9%; and yield of cyclohexene, 6.0%.

EXAMPLES 2 TO 4

Using the catalyst produced in Example 1, partial hydrogenation of benzene was carried out for 3 hours in the same manner as in Example 1 except that 0.5 g each of the metal sulfates shown in Table 1 was used as an additive in place of $Li_2SO_4 \cdot H_2O$.

After completion of the reaction, the oily layer was taken out, and the product was analyzed by gas chromatography to obtain the result shown in Table 1.

TABLE 1

| Example | Additive | Conversion of benzene (%) | Selectivity of cyclo-hexene (%) | Yield of cyclohexene (%) |
|---|---|---|---|---|
| 2 | $CoSO_4 \cdot 7H_2O$ | 69.3 | 41.9 | 29.0 |
| 3 | $FeSO_4 \cdot 5H_2O$ | 60.6 | 23.9 | 14.5 |
| 4 | $ZnSO_4 \cdot 7H_2O$ | 64.6 | 32.8 | 21.2 |

COMPARATIVE EXAMPLES 2 TO 8

Using the catalyst produced in Example 1, procedure was carried out in the same manner as in Example 1 except that 0.5 g each of metal sulfates shown in Table 2 was used in place of 0.5 g of $Li_2SO_4 \cdot H_2O$. The result is shown in Table 2.

TABLE 2

| Comparative Example | Additive | Conversion of benzene (%) | Selectivity of cyclo-hexene (%) | Yield of cyclohexene (%) |
|---|---|---|---|---|
| 2 | $Na_2SO_4 \cdot 7H_2O$ | 91.5 | 5.6 | 5.1 |
| 3 | $CaSO_4 \cdot 2H_2O$ | 94.5 | 7.6 | 7.2 |
| 4 | $Cr_2(SO_4)_3 \cdot 15H_2O$ | 33.4 | 19.7 | 6.6 |
| 5 | $MnSO_4 \cdot 5H_2O$ | 88.7 | 7.4 | 6.6 |
| 6 | $NiSO_4 \cdot 6H_2O$ | 11.4 | 35.9 | 4.1 |
| 7 | $CuSO_4 \cdot 5H_2O$ | 10.2 | 45.2 | 4.6 |
| 8 | $Al_2(SO_4)_3$ | 45.2 | 8.9 | 4.0 |

EXAMPLE 5

To a 500 cc eggplant-form flask were added 200 cc of water, 0.190 g of $RuCL_3 \cdot 3H_2O$ and 0.212 g of $Co(NO_3)_2 \cdot 6H_2O$, and the metal salts were dissolved in the water. After adding 3.6 g of $BaSO_4$, the flask was mounted on a rotary evaporator. The $BaSO_4$ was impregnated with the aqueous solution with stirring at room temperature for 1 hour, and then at 60° C. for 1 hour. Thereafter, water was evaporated at 80° C. under reduced pressure.

The dried-up product obtained was filled in a Pyrex glass tube of 5 mm in inside diameter, heated to 200° C. while passing hydrogen gas therethrough at a rate of 100 ml/min and kept at this temperature for 4 hours to activate the catalyst. The composition of the catalyst obtained was 2% $Ru-Co(1:1)/BaSO_4$.

15 cc of water was added to a 100 ml stainless steel autoclave of which the atmosphere was thoroughly replaced by argon in advance, and then 200 mg of the above catalyst and 15 cc of benzene were added in this order. Thereafter, hydrogen gas was introduced, and reaction was carried out at 180° C. for 1.5 hours with stirring under a reaction pressure of 4.0 MPa. After completion of the reaction, the oily layer was taken out, and the product was analyzed by gas chromatography to obtain the result: Conversion of benzene, 82.8%; selectivity of cyclohexene, 26.4%; and yield of cyclohexene, 21.9%.

Hereupon, a reaction product other than cyclohexene was cyclohexane only.

EXAMPLES 6 to 11

A catalyst was prepared in the same manner as in Example 5 except that cobalt and iron were used as metal components to be co-supported, and that the amounts of the metals and ruthenium supported were changed.

Partial hydrogenation was also carried out in the same manner as in Example 5 to obtain the result shown in Table 3.

TABLE 3

| Example | Catalyst* | Reaction time (hr) | Conversion of benzene (%) | Selectivity of cyclo-hexene (%) | Yield of cyclohexene (%) |
|---|---|---|---|---|---|
| 6 | 0.5% Ru—Co(1:1)/$BaSO_4$ | 5 | 84.3 | 24.9 | 21.0 |
| 7 | 1% Ru—Co(1:2)/$BaSO_4$ | 2 | 80.9 | 28.6 | 23.1 |
| 8 | 0.5% Ru—Fe(1:2)/$BaSO_4$ | 6 | 84.5 | 24.9 | 21.0 |
| 9 | 2% Ru—Fe(1:1)/$BaSO_4$ | 1.5 | 83.5 | 28.5 | 23.8 |
| 10 | 2% Ru—Fe(1:2)/$BaSO_4$ | 2 | 79.4 | 25.7 | 20.4 |
| 11 | 5% Ru—Fe(1:2)/$BaSO_4$ | 1 | 77.1 | 29.1 | 22.4 |

*$RuCl_3 \cdot 3H_2O$, $Co(NO_3)_2 \cdot 6H_2O$ and $Fe(NO_3)_3 \cdot 9H_2O$ were used as materials for the metal components.

COMPARATIVE EXAMPLE 9

To a 500 cc eggplant-form flask were added 200 cc of water, 0.190 g of $RuCl_3 \cdot 3H_2O$ and 0.294 g of $Fe(NO_3)_3 \cdot 9H_2O$, and the metal salts were dissolved in the water. After adding 3.6 g of $\gamma-Al_2O_3$, the flask was mounted on a rotary evaporator. The $\gamma-Al_2O_3$ was impregnated with the aqueous solution with stirring at room temperature for 1 hour, and then at 60° C. for 1 hour. Thereafter, water was evaporated at 80° C. under reduced pressure. Subsequently, 2% $Ru-Fe(1:1)/\gamma-Al_2O_3$ catalyst was prepared in the same manner as in Example 5. Partial hydrogenation of benzene was then carried out for 1 hour in the same manner as in Example 5 to obtain the result: Conversion of benzene, 69.4%; selectivity of cyclohexene, 10.7%; and yield of cyclohexene, 7.4%.

EXAMPLE 12

To a 500 cc eggplant-form flask were added 200 cc of water, 0.190 g of $RuCl_3 \cdot 3H_2O$, 0.212 g of $Co(NO_3)_2 \cdot 6H_2O$ and 0.018 g of $Cu(NO_3)_2 \cdot 3H_2O$, and the metal salts were dissolved in the water. Subsequently, 2% Ru-Co-Cu(1:1:0.1)/$BaSO_4$ catalyst was prepared in the same manner as in Example 5, and partial hydrogenation of benzene was carried out for 2 hours to obtain the result: Conversion of benzene, 74.1%; selectivity of cyclohexene, 30.1%; and yield of cyclohexene, 22.3%.

EXAMPLES 13 to 18

In the same manner as in Example 12, catalysts were prepared in which the composition of metal components supported on a $BaSO_4$ carrier was as shown in Table 4 and the rate of ruthenium supported was 2%, and partial hydrogenation of benzene was carried out using the catalyst obtained. The result is shown in Table 4.

TABLE 4

| Example | Ratio of metal atoms supported* | Reaction time (hr) | Conversion of benzene (%) | Selectivity of cyclo-hexene (%) | Yield of cyclohexene (%) |
|---|---|---|---|---|---|
| 13 | Ru—Co—Cu(1:1:0.5) | 4 | 62.1 | 32.0 | 19.9 |
| 14 | Ru—Co—Cu(1:2:0.1) | 2.5 | 69.8 | 32.2 | 22.5 |
| 15 | Ru—Co—Ag(1:1:0.1) | 2 | 78.4 | 26.6 | 20.8 |
| 16 | Ru—Fe—Cu(1:1:0.1) | 2 | 74.3 | 28.6 | 21.2 |
| 17 | Ru—Fe—Cu(1:2:0.1) | 2.5 | 71.1 | 30.6 | 21.8 |
| 18 | Ru—Fe—Ag(1:1:0.1) | 2 | 80.7 | 24.9 | 20.1 |

*$RuCl_3.3H_2O$, $Co(NO_3)_2.6H_2O$, $Fe(NO_3)_3.9H_2O$, $Cu(NO_3)_2.3H_2O$ and $AgNO_3$ were used as materials for the metal components.

EXAMPLES 19 and 22

Partial hydrogenation of benzene was carried out in the same manner as in Example 5 using 200 mg of 2% Ru-Fe(1:1)/$BaSO_4$ prepared in Example 9 and 0.5 g each of the metal sulfates shown in Table 5 as an additive. The result is shown in Table 5.

TABLE 5

| Example | Additive | Reaction time (hr) | Conversion of benzene (%) | Selectivity of cyclo-hexene (%) | Yield of cyclo-hexene (%) |
|---|---|---|---|---|---|
| 19 | $CoSO_4.7H_2O$ | 3 | 87.8 | 43.2 | 37.9 |
| 20 | $Li_2SO_4.H_2O$ | 3 | 84.5 | 38.5 | 32.5 |
| 21 | $FeSO_4.5H_2O$ | 3.5 | 80.7 | 39.5 | 31.9 |
| 22 | $ZnSO_4.7H_2O$ | 4 | 78.9 | 45.2 | 35.7 |

EXAMPLES 23 to 27

Partial hydrogenation of benzene was carried out in the same manner as in Example 5 using 200 mg each of the catalysts prepared in Examples 12 to 15 and 17 and 0.5 g of $CoSO_4.7H_2O$ as an additive. The result is shown in Table 6.

TABLE 6

| Example | Ratio of metal atoms supported | Reaction time (hr) | Conversion of benzene (%) | Selectivity of cyclo-hexene (%) | Yield of cyclohexene (%) |
|---|---|---|---|---|---|
| 23 | Ru—Co—Cu(1:1:0.1) | 3.5 | 75.8 | 53.4 | 40.5 |
| 24 | Ru—Co—Cu(1:1:0.5) | 6 | 62.6 | 55.4 | 34.7 |
| 25 | Ru—Co—Cu(1:2:0.1) | 3 | 83.8 | 45.1 | 37.8 |
| 26 | Ru—Co—Ag(1:1:0.1) | 3 | 84.8 | 44.2 | 37.4 |
| 27 | Ru—Fe—Cu(1:2:0.1) | 3.5 | 77.1 | 49.7 | 38.3 |

EXAMPLE 28

15 cc of water was added to a 100 ml stainless steel autoclave of which the atmosphere was thoroughly replaced by argon in advance, and then 200 mg of 2% Ru-Co(1:1)/$BaSO_4$ catalyst prepared in Example 5 and 15 cc of toluene were added in this order. Thereafter, hydrogen gas was introduced, and partial hydrogenation of toluene was carried out at 180° C. for 2 hours with stirring under a reaction pressure of 4.0 MPa.

After completion of the reaction, the product was analyzed by gas chromatography to obtain the result: Conversion of toluene, 72.5%; selectivity of methylcyclohexene, 30.2%; and yield of methylcyclohexene, 21.9%.

Hereupon, the resulting methylcyclohexene was a mixture of 1-methylcyclohexene, 3-methylcyclohexene and 4-methylcyclohexene.

EXAMPLE 29

Partial hydrogenation of toluene was carried out for 5 hours in the same manner as in Example 28 using 200 mg of a 2% Ru-Fe-Cu(1:1:0.1)/$BaSO_4$ catalyst prepared in Example 17 and 1.0 g of $CoSO_4.7H_2O$, to obtain the following result: Conversion of toluene, 64.8%; selectivity of methylcyclohexene, 40.5%; and yield of methylcyclohexene, 26.2%. Hereupon, the resulting methylcyclohexene was a mixture of a 1-methylcyclohexene, 3-methylcyclohexene and 4-methylcyclohexene.

What is claimed is:

1. A method for producing cycloolefin which comprises partial hydrogenation of aromatic hydrocarbons with hydrogen gas in the presence of a catalyst composed of barium sulfate which is a carrier as well as ruthenium and at least one metal selected from the group consisting of iron, cobalt, silver and copper supported on said barium sulfate, and water.

2. A method according to claim 1, wherein the rate of ruthenium supported is 0.01 to 20 wt. %.

3. A method according to claim 1 using a catalyst composed of ruthenium and iron or cobalt supported on barium sulfate, the atomic ratio of iron or cobalt to ruthenium being 0.1–15.0:1.

4. A method according to claim 1 using a catalyst composed of ruthenium and copper or silver supported on barium sulfate, the atomic ratio of copper or silver to ruthenium being 0.05–50:1.

5. A method according to claim 1, wherein the amount of water added is 0.01 to 10 times by volume based on the aromatic hydrocarbon.

6. A method according to claim 1, wherein the reaction temperature is 50° to 250° C.

7. A method according to claim 1, wherein the aromatic hydrocarbon is benzene or toluene.

8. A method for producing cycloolefins which comprises partial hydrogenation of aromatic hydrocarbons with hydrogen gas in the presence of a catalyst composed of barium sulfate which is a carrier as well as ruthenium and at least one metal selected from the group consisting of iron, cobalt, silver and copper supported on said barium sulfate, an additive comprising the sulfate of at least one metal selected from the group consisting of lithium, cobalt, iron and zinc, and water.

9. A method according to claim 8, wherein the rate of ruthenium supported is 0.01 to 20 wt. %.

10. A method according to claim 8 using a catalyst composed of ruthenium and iron or cobalt supported on barium sulfate, the atomic ratio of iron or cobalt to ruthenium being 0.1–15.0:1.

11. A method according to claim 8 using a catalyst composed of ruthenium and copper or silver supported on barium sulfate, the atomic ratio of copper or silver to ruthenium being 0.05–50:1.

12. A method according to claim 8, wherein the amount of water added is 0.01 to 10 times by volume based on the aromatic hydrocarbon.

13. A method according to claim 8, wherein the atomic ratio of the additive comprising a metal sulfate to ruthenium is 1:1 to 500:1.

14. A method according to claim 8, wherein the reaction temperature is 50° to 250° C.

15. A method according to claim 8, wherein the aromatic hydrocarbon is benzene or toluene.

16. A method for producing cycloolefins which comprises partial hydrogenation of aromatic hydrocarbons with hydrogen gas in the presence of a catalyst composed of barium sulfate which is a carrier and ruthenium supported thereon, an additive comprising the sulfate of at least one metal selected from the group consisting of lithium, cobalt, iron and zinc, and water.

17. A method according to claim 16, wherein the rate of ruthenium supported is 0.01 to 20 wt. %.

18. A method according to claim 16, wherein the amount of water added is 0.01 to 10 times by volume based on the aromatic hydrocarbon.

19. A method according to claim 16, wherein the atomic ratio of the additive comprising a metal sulfate to ruthenium is 1:1 to 500:1.

20. A method according to claim 16, wherein the reaction temperature is 50° to 250° C.

21. A method according to claim 16, wherein the aromatic hydrocarbon is benzene or toluene.

* * * * *